United States Patent [19]
DeLuca et al.

[11] Patent Number: 5,955,086
[45] Date of Patent: Sep. 21, 1999

[54] OREGANO FOR THE TREATMENT OF INTERNAL PARASITES AND PROTOZOA

[75] Inventors: Daryl L. DeLuca, Sugar Land; William S. Sparks, Bellaire; Robert A. Ronzio, Houston; Denis R. DeLuca, Katy, all of Tex.

[73] Assignee: Biotics Research Corporation, Rosenberg, Tex.

[21] Appl. No.: 09/099,580

[22] Filed: Jun. 18, 1998

[51] Int. Cl.$^6$ .......................... A01N 65/00; A01N 63/00; A01N 31/08; A61K 9/22

[52] U.S. Cl. ................ 424/195.1; 424/464; 424/468; 424/93.4; 424/93.45; 514/731

[58] Field of Search .................. 424/195.1, 406, 424/408, 468, 481, 464, 93.4, 93.45; 514/731

[56] References Cited

FOREIGN PATENT DOCUMENTS

WO 96/37210  11/1996  WIPO ........................... A61K 35/78
WO 97/01348  1/1997  WIPO ........................... A61K 35/78

OTHER PUBLICATIONS

Hocquemiller et al. J. Natural Products. 54(2), pp. 445–452. (Mar. 1991).

Pietrusko, R.G. Amer. J. Hospital Pharmacy. 36(6), pp. 757–767. Jun. 1979). Abstract only.

Nnochiri, E. Medical Parasitology in the Tropics. pp. 6–126. Oxford University Press, London. (1975). No month given.

Udkow et al "*Blastocystis hominis*: Prevalence in Asymptomic . . . "JID:168 pp. 242–244 (Jul. 1993).

Zierdt "*Blastocystis hominis*—Past and Future" Clin. Microbio. Rev (Nov. 1991): v 4 pp. 61–79.

Wilson et al "*Blastocystis Hominis* Infection: Signs and Symptoms . . . " Military Med (Sep. 1990) v 155 pp. 393–395.

Waghorn et al "Clinical Significance of *Blastocystis hominis* "(Mar. 1991) Lancet v 337 p. 609.

O'Gorman et. al"Prevalence and Characteristics of *Blastocystis hominis* . . . " Clin Ped (Feb. 1993), Feb pp. 91–96.

Garavelli et al "Blastocystosis: A New Disease . . . " Int. J of STD & AIDS, 1990, v 1 pp. 134–135, No Month Given.

Solomons et. al "Nutritional Implications of Parasitic Infections" Nut. Rev., v 39 pp. 149–161. (Apr. 1981).

Physicians Desk Refenence, 1995 No Month Found "Atabrine" "Flagyl" "Yodoxin," pp. 1114, 2199, 2322–2323.

Sivropoulou et al "Antimicrobial . . . Activities of Origanum . . . " J Ag Food Chem, 1996, 44, 1202–1205, No Month Found.

Azzouz et al "Comparative Antimycotic Effects of Selected Herbs . . . " J of Food Protect. v 45 (Dec. 1982) pp. 1298–1301.

Conner et al "Effects of Essential Oils . . . " J of Food Sci 1984, v 49 pp. 429–434, No Month Found.

Lagouri et al "Nutrient Antioxidants in Oregano" Int. J of Food Sci & Nut. 1996 v 47 pp. 493–497, No Month Found.

Belaiche "Traité de Phytotherapy et d'Aromatheapie" 1979, Maloine S.A., Paris pp. 92–101, No Month Found.

Stiles et al "The Inhibition of *Candida Albicans* by Oregano" 1995, J of App. Nut. vol. 47 pp. 96–102, No Month Found.

Ponce–Macotela "Efecto antigiardiasico in vitro de 14 extractos de plantas" (Oct. 1994) Rev Invest Clin v 46 343–7.

*Primary Examiner*—Kathleen K. Fonda
*Attorney, Agent, or Firm*—John R. Casperson

[57] ABSTRACT

The use of oregano and its essential oil in the treatment of, and prophylactic use for, parasitic infections is described.

18 Claims, No Drawings

OREGANO FOR THE TREATMENT OF INTERNAL PARASITES AND PROTOZOA

BACKGROUND OF THE INVENTION

The invention relates to the treatment of internal parasites and protozoa, especially in humans. In one aspect, the invention relates to an improved treatment of parasitic, including protozoic, infections in humans using an extract of oregano.

Parasitic infections have a long history as a cause of disease in humans and animals. These include protozoan parasites such as extra-intestinal amoebas, toxoplasmas and trichomonas. In addition to protozoa, other human parasites include helminths such as roundworm, pinworm, hookworm, shisasomes and tapeworm. Pathogenic protozoa, such as *Giardia lamblia, Entamoeba histolytica, Dientamoeba fragilis, Cryptosporidium parvum, Cyclospora cayetanensis* as well as *Blastocystis hominis*, are recognized as pathogenic organisms. See Gugliemetti P et al, Family outbreak of *Blastocystis hominis* associated with gastroenteritis, Letter, Lancet 1989,vol. 2, 1394; Udkow MP et al., *Blastocystis hominis*: Prevalence in asymptomatic versus symptomatic hosts, JID 1993, 168:242–4; Zierdt CH, *Blastocystis hominis*, Past and Future, Clin Microbiol Rev 1991; 4:61–79; Wilson K, et al., *Blastocystis hominis* infection: signs and symptoms in patients at Wilford Hall Medical Center, Military Med 1990; 155:394–6; Waghorn DJ, et al: Clinical significance of *Blastocystis hominis*. Letter. Lancet 1991: 337:609; O'Gorman M. et al: Prevalence and characteristics of *Blastocystis hominis* infection in children, Clinical Pediatrics, 1993; 32:91–96.

Certain intestinal parasites are not generally considered to cause symptoms in those with robust immune systems. In this category are *Entamoeba nana, E. hartmanni, Entamoeba coli, Endolimax nana* and *Enteromonas hominis*. Nonetheless, the presence of multiple intestinal parasites may indicate a compromised immune system, imbalanced gut flora and/or abnormal digestive function, such as hypochlorhydria. Treatment is at the discretion of the physician. See Garaveli PL et al. , "Blastocystis: a new disease in the acquired immunodeficiency syndrome," International J STD & AIDS 1990; 1:134–135.

Many parasites that reside in the gastrointestinal tract cause gastrointestinal signs and symptoms, such as abdominal pain, bloating, diarrhea, and secondary carbohydrate intolerances including lactose intolerance and unexplained weight loss. See Jones JE, Signs and symptoms of parasitic disease, Primary Care 1991; 12:1–12. In some cases infection by intestinal parasites becomes self-limiting; in other cases parasites can cause chronic infection with intermittent symptoms that can persist indefinitely until treated. Parasites such as *E. histolytica* can penetrate the gut mucosal barrier, leading to infections of specific organs or to systemic infection. These may be more difficult to eliminate.

The prevalence of various parasitic infections in the U. S. reflects multiple factors. Lifestyle, purity of domestic water supplies, and state of an individual's immune system are keys. The fecal-oral route of infection is common and poor hygiene among food handlers has increased the prevalence in some areas. Contamination of municipal water supplies by agricultural run-off, together with ineffective water treatment have caused localized epidemics.

Treatment of parasitic infections typically relies on a series of medications including tinidazole, metronidazole, quinacrine hydrochloride, iodoquinol and similar compounds. These can have significant side effects, as cited in the Physicians'Desk Reference , $49^{th}$ Edition, Medical Economics Data Production Co. 1995,including pages 1114, 2199, 2322–2324.

Botanical preparations offer an alternative approach to treatment. Herbs have been used in folk medicine for centuries for diarrhea and gastrointestinal upsets. However, culinary herbs are cited for their antioxidant, antibacterial and antifungal properties most often in the context of food preservation, but not as antiparasitics. See Azzouz MA et al. , "Comparative antimycotic effects of selected herbs, spices, plant components and commercial antifungal agents," J Food Protection 1982; 45:1298–1301; Conner DE, et al. , Effects of essential oils from plants on growth of food spoilage yeasts, J Food Science 1984; 49: 429–34; Lagouri V et al. , Nutrient antioxidants of oregano. Int J Food Sci Nutr 1996; 47:493–7.

In particular, oregano (*Oreganum vulgare*, Mediterranean oregano) a common culinary herb, and its associated essential oil have been shown to inhibit the growth of many kinds of bacteria. See Belaiche P, Traite de Phytotherapie et d'Armoatherapie, Tome 1. L'Aromatogramme, Maloine SA Editeur, 1979, pp 92–100.

In addition, the oil of oregano is a potent inhibitor of yeast and fungi, including the potential pathogen, *Candida albicans*. See Stiles JC et al. , The inhibition of *Candida albicans* by oregano, J Applied Nutr 1995; 47:96–102; Sivropoulou A et al. , Antimicrobial and cytotoxic activities of Origanum essential oils, J Agric Food Chem 1995; 44: 1202–1205.

There are no previous reports documenting the use of oregano (*Oreganum vulgare*) in the treatment of parasites in the scientific literature. A single report cites "oregano" in the context of inhibition of *Giardia lamblia* trophozytes in culture. See Ponce-Macotela M et al. , "Efecto antigiardiasico in vitro de 14 extractos des plantas", Rev Invest Clin 1994; 46:343–7. Ponce-Macotela et al studied extracts of plants typically used in Mexico as antidiarrheals and/or antiparasitics. However, the particular plant they refer to as oregano was *Lipia beriandieri*, which belongs to the *Lippia genera*, and not *Oreganum vulgare*. These investigators did not systematically study patients to determine whether in fact parasites could be eradicated by treatment.

OBJECTS OF THE INVENTION

An object of this invention is to provide a therapeutic treatment for human and other internal parasitic infections in order to eradicate parasites without reliance on standard medications. Internal parasites in question include all known types, including protozoa such as intestinal amoeba and extra-intestinal amoeba, giardia, as well as various types of helminths.

SUMMARY OF THE INVENTION

We have found that oregano and its direct products including the essential oil is useful for the treatment and/or prevention of internal parasitic infections in humans and domestic animals.

We have determined that a composition of matter comprising oil of oregano in an emulsified form, a pharmaceutically compatible carrier; and a dissolution-delaying agent, is particularly effective for such use.

The human (or animal) which has the internal parasitic infection is treated with an extract of oregano in a manner to bring an effective amount of the extract or a metabolic product from the extract into contact with the parasites. The above described composition is especially effective for this application when administered orally. The treatment is continued for a period of time sufficient to reduce the population of such parasites, typically several days.

Extract of oregano can also be used to prevent an infestation of internal parasites in an animal (or human) which is exposed to such internal parasites by orally administering to such animal an amount of a extract of oregano which is effective to prevent such infestation, typically on a daily basis during the period of exposure or potential exposure. The above described composition is highly effective for this purpose as well.

It further appears to us that the effective moiety in the above described composition is the chemical compound carvacrol. In a further embodiment of the invention, we thus propose to treat a mammal having a symptomatic infestation of internal parasites by orally administering the chemical compound carvacrol in a sustained release form as a plurality of divided daily doses until the mammal becomes asymptomatic of internal parasite infestation.

DETAILED DESCRIPTION OF THE INVENTION

According to the present invention, it has now been discovered that oil of oregano administered orally, particularly after emulsification and tableted in a sustained release form, is capable of reducing the quantity and number of intestinal parasites detected by stool analysis and in certain instances totally eradicating intestinal parasites. Because intestinal flora are altered by this treatment, supplementation with lactic acid-forming bacteria, especially *Lactobacillus acidophilus* and Bifodobacteria, can help return the gut bacteria to normal.

The method may generally be applied to humans or animals having an internal infection of parasites. The term "parasite" is intended to encompass protozoa, including amoebae and flagellates, as well as multicellular parasites, such as helminths (roundworms) and platyhelminthes (flatworms), which reside within the animal host. The invention is especially applicable to intestinal parasites.

Intestinal amoebae include *Entamoeba hartmanni, Blastocystis hominis* and *Endolimax nana*, as well as *Entamoeba histolytica*, which is a well known cause of dysentery.

Intestinal flagellates include *Giardia lamblia, Dientamoeba fragilis*, and *Trichonomas hominis*.

Other intestinal protozoa that cause food-associated parasitic infections include *Entamoeba polecki, Sarchocystis hominis*, and *Toxoplasma gondii* (from food and water contaminated by cat feces).

Intestinal helminths include parasites that can be transmitted by eating raw fish and meat.

Nematodes (roundworms) include Anasakis species, Ascaris species, *Trichinella spiralis* (trhininosis) and Ancyclostoma species (hookworm), *Trichuris trichiura* (whipworm), and *Enterobius vermicularis* (pinworm).

Cestodes are tapeworms. These include *Diphyllobothrium latum*, Spirometra species, Taenia species (from poorly cooked pork and beef) and Hymenolepsis species (from grains contaminated by meal worms infected by rodent feces).

Trematodes are flukes. *Clonorchis sinensis, Opisthorchis viverrini* and *O. flineus* represent liver flukes. *Schistomsoma haematobium* and related species are well established pathogenic organisms.

Intestinal flukes include *Heterophyes heterophyes, Metagoniumus yokogawai*, and *Echinistoma ilocaneum*.

Other types of parasites which may be treated in accordance with the invention include Trypansomes carried by the Tsetse fly, and Leishmania species, carried by blood-sucking organisms, as well as *Trichomonas vaginalis*, which is sexually transmitted and is detected in a manner similar to intestinal parasites.

Patients are treated with preparations of the oil of oregano so that the oral dosage is in the range of 50 mg to 500 mg or more daily for several weeks, typically four to six weeks, until analysis, typically a fecal analysis, reveals the absence of the parasite in question. In a clinical trial of the invention, after 14 days of treatment with oil of oregano, patients were further administered Lactozyme, a preparation of *Lactobacillus acidophilus* and *Bifidobacterium bifidus* from Biotics Research Corporation, to provide a total 10 to 12 million organisms three times daily, just before meals.

The composition employed contained oil of oregano in an emulsified form, a pharmaceutically compatible carrier, and a dissolution-delaying agent.

The oregano content was adjusted so that the tablets which contained in the range of 50 to 500 mg of oil of oregano. It is believed that the oil of oregano should contain at least 25% by weight of carvacrol for good results, preferably at least 50% by weight.

Although the makeup of the tablets can vary over a wide range, it is believed that employing in the range of 1% to 10% by weight of oil of oregano, in the range of 20% to 80% by weight of carrier; and in the range of 5% to 20% by weight of dissolution delaying agent will generally yield good results.

The oil of oregano can be emulsified with a variety of emulsifying agents. Gum Arabic has been used with good results. Where gum arabic is employed as the emulsifying agent, the tablet will generally contain in the range of 1% to 10% by weight of gum arabic. Where the tablet contains a friction-reducing agent to facilitate tableting, in the range of 0. 5% to 5% by weight of friction reducing agent will provide good results.

The preferred dissolution delaying agent comprises hydroxypropylmethylcellulose, because it is readily available and its use permits the rate of dissolution to be varied by adjusting the amount of hydroxypropylmethylcellulose present. The rate of dissolution can be adjusted to provide continuous release of the oil of oregano over a period which is generally several hours. It is believed that sustained release of the oregano after ingestion over a time period in the range of about 3 to about 24 hours, preferably over a time period in the range of about 6 to about 1 8 hours, and more preferably in the range of about 8 to about 15 hours will provide good results. The tablet will also generally contain a pharmaceutically accepted carrier. Dicalcium phosphate has been used for this purpose with good results.

Preferred friction reducing agents can be selected from the group consisting of magnesium stearate, calcium stearate, stearic acid and silicon dioxide. Magnesium stearate is most preferred because it has been tested with good results.

If desired, the tablets can contain potassium sorbate, which can serve as a marker to facilitate measuring the dissolution rate of the tablet and also has antifungal properties. When used, an amount of potassium sorbate in the range of 2% to 20% by weight will provide good results.

The most preferred tablets for use in the invention consist essentially of in the range of 2 ½% to 7 ½% by weight of oil of oregano, in the range of 50% to 70% by weight of dicalcium phosphate, in the range of 5% to 20% by weight of hydroxypropylmethylcellulose, in the range of 2 ½% to 7 ½% by weight of gum arabic, in the range of 2% to 4% by weight of magnesium stearate, and in the range of 5% to 15% by weight of potassium sorbate, because tablets containing ingredients within these narrow ranges have been tested with good results.

Animals, particularly mammals, including humans, can be treated for internal parasites in accordance with the invention. It is believe that this embodiment of the invention will its greatest utility for treating humans and domestic mammals for intestinal parasites, especially protozoic parasites.

It is generally desirable to first perform a confirmatory test on the animal suspected of having a population of internal parasites and to be treated in accordance with this aspect of the invention. Animals for which the confirmatory test is positive are treated with an extract of oregano in a manner to bring an effective amount of the extract, or a metabolic product from the extract, into contact with the parasites. The treatment is continued for a period of time sufficient to reduce the population of such parasites.

The extract of oregano generally is taken from the leaves of an oregano plant. The preferred oregano plant comprises *Oreganum vulgare*, since extracts from this species have been tested with good results and contain high amounts of the presumed active ingredient.

The extract is preferably administered orally and most preferably in a sustained release form. An emulsified form of the extract is most preferred, and the most preferred method is administration orally in an emulsified, tableted, sustained release form. The above described tablets are highly suitable.

A suitable extract is commercially available as oil of oregano. Preferably the oil contains at least 25% by weight of the compound carvacrol, as it is this compound which is believed to be the active ingredient. Most preferably, the oil of oregano contains at least 50% by weight of carvacrol.

Generally speaking, in the range of 100 to 2000 mg of oil of oregano is orally administered daily as a plurality of divided doses, usually in the range of 200 to 1000 mg daily. The daily administration is continued for a period of time in the range of about 1 to about 10 weeks. It is believed desirable to also orally administer naturally occurring gut bacteria on a daily basis during at least the latter part of the treatment period. Desirable naturally occurring gut bacteria include *Lactobacillus acidophilus* and *Bifidobacterium bifidus*.

Oregano can also be used prophylactically, to prevent internal parasite infestation. This aspect of the invention is carried out by orally administering to an animal during a period of potential exposure to internal parasites an amount of a extract of oregano which is effective to prevent the animal from becoming infested by the parasites. The amount of extract of oregano employed is preferably not so high as to cause illness in the animal. Concomitant administration of naturally occurring gut bacteria can reduce the risk of undesirable side effects.

For this purpose, the extract of oregano will generally be administered on a daily basis, preferably as oil of oregano in a sustained release form. The oil of oregano preferably will contain at least 50% by weight of carvacrol. Generally speaking in the range of 10 to 1000 mg of oil of oregano will be administered daily.

Because it appears to us that the chemical compound carvacrol is the active ingredient, we propose to treat a mammal having a symptomatic infestation of internal parasites by orally administering the chemical compound carvacrol in a sustained release form as a plurality of divided daily doses until the mammal becomes asymptomatic of internal parasite infestation. For humans, it is expected that in the range of 10 to 1000 mg of carvacrol will be administered daily.

Clinical results have shown that treatment in accordance with the invention is effective in at least reducing intestinal parasites selected from the group consisting of *Blastocystis hominis, Entamoeba hartmanni, Endolimax nana*, Candida species, Kloeckeri species, and Geotricum species. It is expected that the treatment will also be effective to treat intestinal infestations of protozoan parasites such as extraintestinal amoebas, toxoplasmas and trichomonas, helminths such as roundworm, pinworm, hookworm, shistasomes and tapeworm, pathogenic protozoa, such as *Giardia lamblia, Entamoeba histolytica, Dientamoeba fragilis, Cryptosporidium parvum, Cyclospora cayetanensis* and *Blastocystic hominis, Entamoeba nana, E. hartmanni, Entamoeba coli, Endolimax nana* and *Enteromonas hominis*.

The invention is further illustrated the following example.

EXAMPLE

Preparation of gum arabic solution

A 50% solution of gum arabic is prepared by dissolving 1000 gm of gum arabic into 2000 ml of purified water. Preferably deionized water is used but water may be further purified by filtration and/or distillation. If gum arabic has not been previously heated to remove active spores, the gum arabic solution should be heated. Typically 90° C. will inactive spores which can cause microbial contamination of solution. If heating has been carried out, the solution is then cooled to room temperature. If desired, the gum arabic solution may be further stabilized with suitable antimicrobial agents such as sodium benzoate. The solution thus prepared is typical of gum arabic solutions used in pharmaceutical manufacturing.

The oil of oregano

Commercially available oil of oregano is suitable for use in the invention. Because it is thought that the active antibiological (antifungal, antimicrobial and antiparasitic) agent in oregano oil is the compound carvacrol, the oil of oreganum should be at least 65% carvacrol. Most commercially available oils of *Oreganum vulgare* meet this requirement.

Emulsification of gum arabic solution with oil of oregano

The above described gum arabic solution is emulsified with 1000 gm of the selected oil of oregano using a high shear mixer and slow addition of oil of oreganum. When fully emulsified the preparation will be one part oil of oregano: one part gum: two parts water. The emulsification will be an oil in water emulsion with an oil particle size ranging (95% of all particles) between 0.5 to 1.0 microns.

Concentration

Various pharmaceutical methods of removing the water from the emulsified oil of oregano prepared as above may be used. Granulation is one such method. Spray drying is also suitable.

Using a granulation method the emulsion solution would be added to a suitable carrier. The carrier should be such that it does not alter the biological properties of the preparation. As such, cellulose or dicalcium phosphate are preferred. For example, using a hobart blender, one kg of oregano oil (4 kg of emulsified solution) is added to 11.9 kg of dicalcium phosphate dihydrate unmilled. This mixed preparation is then added to trays typical of those used for granulation in pharmaceutical production. Using this example the granulation mixture prepared would be added to four paper lined trays (2'×3'). The trays would then be placed in a rack which is then rolled into a drying room. This preparation should be allowed to dry at a minimum temperature of 104° F. until dry. Typically the drying process will last 72 hours at this temperature. The dried granulation is removed and milled through a screen size of between 20 and 60 mesh.

Tableting

The granulated material as described above contains 11. 9 kg calcium phosphate, 1 kg oil of oregano and 1 kg of gum arabic. This granulation is blended with (1) a suitable dissolution-delaying agent to delay dissolution and (2) a suitable friction-reducing agent that reduces friction during tableting.

The preferred dissolution delaying agent is hydroxypropylmethylcellulose (HPMC), which is an approved food additive. Commercially, this is available from Dow Chemical Company under the trade name Methocel. The most preferred Methocel preparations used are trade named Methocel K4M and Methocel K4M Premium. These preparations have a known chemical composition containing 19–24% methoxyl and 7–12% hydroxypropyl cellulose. This agent is preferred because the rate of dissolution of the final preparation may be controlled by the percentage of Methocel K4M (or K4M Premium) added.

The preferred friction-reducing agent(s) that will reduce tablet friction include magnesium stearate, calcium stearate, stearic acid and silicon dioxide.

A known amount of oil of oregano may be dosed from the above preparation. Typically a 50 mg of oil of oregano tablet is prepared. Using 1 kg of oil of oregano 20, 000 tablets may be made. To prepare a typical batch of 20, 000 tablets the following mixture may be used:

13. 9 kg of emulsified oil of oregano granulation (containing 1 kg oil, 1 kg gum arabic and 11. 9 kg dicalcium phosphate unmilled)

3. 37 kg of Methocel K4M 0. 566 kg of magnesium stearate

To this mixture potassium sorbate may be added. For a batch of 20, 000 tablets, 2. 136 kg of potassium sorbate may be added. The final weight of 20, 000 tablets is 20. 0 kg. This mixture is blended in a suitable mixer used in blending pharmaceuticals.

Using a typical tablet press, a tablet may be pressed having a weight of one gram and containing 50 mg of oil of oregano. The typical B2 tablet press using 2 tons of force will produce a suitable tablet. The dissolution may be controlled by the amount of Methocel to give a desired release of emulsified oil of oregano when taken orally. This release is typically complete after 12 hours.

This preparation has been observed to reduce parasitic populations in human stool samples. This reduction is believed enhanced due to the tremendous increase in surface area possible by emulsification and the delayed release method used.

Clinical

Test Subjects

Fourteen patients were selected who met one or more of the following criteria: gastrointestinal cramping, diarrhea, or diarrhea alternating with constipation, bloating and gas, periodic low grade fever.

Systemic complaints included recurrent headache, fatigue, joint ache, skin disorders and flare up of allergies. Lifestyle risk factors included foreign travel to countries with poor sanitation, institutionalized or communal living conditions, exposure to children who participated in day care, and living in Western counties of the U. S with an out of doors lifestyle. Preliminary lab tests in some instances revealed elevated blood eosinophils.

Regardless of signs and symptoms, all patients were screened for the presence of parasites by a certified, independent clinical laboratory using fecal specimens. In addition, fecal specimens were cultured to detect the presence of yeast and fungi. Samples were scored in terms of prevalence of parasites or yeasts on a scale of +1 to +4. The fourteen patients who tested positive for parasites were then treated according to the following protocol:

Treatment protocol

Patients were administered 5 tablets of the above-described composition (trade named A. D. P. ). from Biotics Research Corporation, three times a day before meals for one week. The A. D. P. preparation provides 50 mg standardized oil of oregano (from the culinary herb, *Oreganum vulgare*) as an emulsified, sustained release form.

After one week of treatment, the dosage of A. D. P. was reduced to three tablets, three times daily. This schedule was continued for another four to six weeks. After 14 days of treatment with oil of oregano, patients were administered Lactozyme, a preparation of *Lactobacillus acidophilus* and *Bifidobacterium bifidus* from Biotics Research Corporation, to provide a total 10 to 12 million organisms three times daily, just before meals.

Results

The results are summarized in Table I.

TABLE I

| | | Before Treatment | | |
|---|---|---|---|---|
| Patient | IDT1 ParaA | T1-FungiA | T1FungiB | After T2ParaA |
| 1. | 2 Blastocystis Hominis (1) | | | Negative |
| 2. | 17 Blastocystis Hominis (4) | Candida (2) Dividing (1) | | Blastocstis Hominis (2), dividing down from 4, no candida |
| 3. | 18 Blastocystis Hominis (2) | Candida (1) | Kloeckeri (1) | Blastocyst-ishominis (1), down from 2, no candida |
| 4. | 19 Blastocystis Hominis (1) | Candida (4) dividing (2) | | Negative |
| 5. | 20 Entamoeba Hartmanni trophozoites | Candida (1) | | Negative |
| 6. | 21 Blastocystis Hominis (1) | Candida albicans (1) | Geotrichum (1) | Negative |
| 7. | 22 Blastocystis Hominis (1) | Candida (2); dividing (1) | Geotrichum (1) | Negative |
| 8. | 23 Endolimax nana cysts (2), e. Nana | Candida (1) | Geotrichum (3) | Negative |
| 9. | 24 Entamoeba Hartmanni trophozoites (1) | Candida (1) | Geotrichum (1) | Negative |
| 10. | 26 Blastocystis Hominis | Candida (1) | Kloeckeri (1) | refused retest |
| 11. | 27 Blastocystis Hominis | Candida (1) | | Blastocystis Hominis (1), down from 2, No candida |
| 12. | 30 Blastocystis Hominis (1) | | | Negative |

TABLE I-continued

| | | Before Treatment | | | |
|---|---|---|---|---|---|
| Patient | IDT1 ParaA | T1-FungiA | T1FungiB | After T2ParaA | |
| 13. | 31 Entamoeba Hartmanni (1) | Candida (1), dividing (1) | | Pending | |
| 14. | 32 Entamoeba Hartmanni (1) | | | Pending | |

Of the patients tested, 14 were positive for parasites at the beginning of the study; 11 of these completed the protocol and all testing. Positive results were obtained in 11/11 patients.

Eight of the patients initially found to have parasites tested negative after treatment according to the oil of oregano protocol. Parasites were eradicated in 72. 7% (8/11) of the test population. This included five patients who initially had *Blastocystis hominis*, two patients with *Entamoeba hartmanni* and one patient with *Endolimax nana*.

In addition, five patients initially tested positive for Candida species and four tested positive for Geotricum. After treatment, none of these patients tested positive for these organisms.

Three patients of the test group (27. 3%, 3/11) still tested positive for parasites after treatment, however the parasite scores dropped after oil of oregano treatment. In two patients, the *B. hominis* score dropped from +2 to +1. In another patient with *B. hominis*, the initial score was +4 and after treatment the score was +2. In this group, no Candida or Kloeckeri, initially present, were detected after oil of oregano treatment. We conclude that the treatment protocol decreased the intestinal parasite load in 27. 3% of patients and eradicated all intestinal parasites in 72. 7% of symptomatic patients.

While certain preferred embodiments of the invention have been heretofore described, the invention is not to be construed as so limited, except to the extent such limitations are found in the claims.

We claim the following:

1. A process for reducing or eradicating intestinal amoeba selected from the group consisting of *Entamoeba hartmanni, Blastocystis hominis, Endolimax nana*, and *Entamoeba histolytica* in humans, said process comprising performing a confirmatory test on a human suspected of having a population of such intestinal amoeba;

treating a human for which the confirmatory test is positive with an extract of oregano in a manner to bring an amount of the extract effective to reduce or eradicate said amoeba into contact with the intestinal amoeba; and continuing the treatment for a period of time in a range of about 1 to about 10 weeks sufficient to reduce or eradicate the population of such intestinal amoeba;

wherein the extract is administered orally in an emulsified tableted, sustained release from and comprises carvacrol as in active ingredient.

2. A process as in claim 1 wherein the extract of oregano comprises an extract from the leaves of an oregano plant.

3. A process as in claim 2 wherein the oregano plant comprises *Oreganum vulgare*.

4. A process as in claim 1 wherein the extract is administered in the form of a tablet comprising oil of oregano in an emulsified form;

a pharmaceutically compatible carrier; and a dissolution-delaying agent;

wherein the oil of oregano is emulsified to from an oil in water emulsion with an oil particle size ranging from 0. 5 to 1. 0 microns.

5. A process in claim 4 wherein the tablet further comprises a friction-reducing agent that reduces friction during tableting.

6. A process as in claim 4 wherein the tablet comprises in a range of 1% to 10% by weight of oil of oregano;

in a range of 20% to 80% by weight of carrier; and in a range of 5% to 20% by weight of dissolution delaying agent.

7. A process as in claim 6 wherein the tablet further comprises in a range of 1% to 10% by weight of gum arabic; and in a range of 0. 5% to 5% by weight of friction reducing agent.

8. A process as in claim 6 wherein the dissolution delaying agent comprises hydroxypropylmethylcellulose.

9. A process as in claim 6 wherein the carrier comprises dicalcium phosphate.

10. A process as in claim 6 wherein the friction reducing agent is selected from the group consisting of magnesium stearate, calcium stearate, stearic acid and silicon dioxide.

11. A process as in claim 6 wherein the tablet further comprises in the range of 2% to 20% by weight of potassium sorbate.

12. A process as in claim 1 wherein the extract contains at least 25% by weight of carvacrol.

13. A process as in claim 1 wherein the extract comprises oil of oregano.

14. A process as in claim 13 wherein the oil of oregano contains at least 50% by weight of carvacrol.

15. A process as in claim 14 wherein in a range of 100 to 2000 mg of oil of oregano is orally administered daily as a plurality of divided doses.

16. A process as in claim 15 further comprising orally administering naturally occurring gut bacteria on a daily basis.

17. A process as in claim 16 wherein the naturally occurring gut bacteria include *Lactobacillus acidophilus* and *Bifidobacterium bifidus*.

18. A process as in claim 17 wherein in a range of 10 to 1000 mg of carvacrol is administered to said human daily.

\* \* \* \* \*